(12) United States Patent
Uhlik et al.

(10) Patent No.: US 6,931,942 B2
(45) Date of Patent: Aug. 23, 2005

(54) PANEL BENDING AND TESTING DEVICE (75) Inventors: Joseph R. Uhlik, Madison, WI (US);
Paul Knuteson, Poynette, WI (US);
Darren J. Robertson, Sun Prairie, WI (US)

(73) Assignee: Timberco, Inc., Madison, WI (US)

( * ) Notice: Subject to any disclaimer, the term of this patent is extended or adjusted under 35 U.S.C. 154(b) by 465 days.

(21) Appl. No.: 10/121,474

(22) Filed: Apr. 11, 2002

(65) Prior Publication Data

US 2003/0192385 A1 Oct. 16, 2003

(51) Int. Cl.$^7$ .................................................. G01N 3/20
(52) U.S. Cl. .................................................... 73/853
(58) Field of Search ............................ 73/852, 862.46, 73/862.472, 862.471, 853

(56) References Cited

U.S. PATENT DOCUMENTS

| | | | |
|---|---|---|---|
| 2,032,989 A | | 3/1936 | Kenney et al. |
| 2,131,805 A | | 10/1938 | Howe |
| 3,286,516 A | | 11/1966 | Post |
| 3,937,072 A | | 2/1976 | Huydts et al. |
| 4,326,421 A | | 4/1982 | Pilesi et al. |
| 4,986,132 A | | 1/1991 | Calomino |
| 5,187,987 A | | 2/1993 | Anderson et al. |
| 5,201,424 A | * | 4/1993 | Hain ........................... 209/534 |
| 5,231,882 A | * | 8/1993 | Bertele et al. ................. 73/852 |
| 5,431,061 A | | 7/1995 | Bertelsen et al. |
| 5,616,848 A | * | 4/1997 | Hemingway et al. .......... 73/838 |
| 5,699,274 A | * | 12/1997 | Starostovic, Jr. ............. 702/113 |
| 5,712,431 A | | 1/1998 | Vilendrer |
| 6,053,052 A | * | 4/2000 | Starostovic ................... 73/851 |
| 6,381,546 B1 | * | 4/2002 | Starostovic ................... 702/36 |
| 6,505,129 B2 | * | 1/2003 | Starostovic et al. ........... 702/36 |

OTHER PUBLICATIONS

The American Society for Testing and Materials; Standard Test Methods for Structural Panels In Flexure; pp. 422–433; Jul. 2000; USA.

Color Photograph; Photo 2; Publicly disclosed prior to Apr. 11, 2001.

Color Photograph; Photo 3; Publicly disclosed prior to Apr. 11, 2001.

Color Photograph; Photo 4; Publicly disclosed prior to Apr. 11, 2001.

* cited by examiner

*Primary Examiner*—Edward Lefkowitz
*Assistant Examiner*—Jewel V. Thompson
(74) *Attorney, Agent, or Firm*—Michael Best & Friedrich LLP (57) ABSTRACT

A panel testing device includes a frame, a first roller assembly pivotally mounted to the frame including a first roller and a second roller spaced apart from and substantially parallel to the first roller. The panel testing device also includes a second roller assembly pivotally mounted to the frame having a third roller and a fourth roller spaced apart from and substantially parallel to the third roller. The device is configured such that the first and third rollers may be engaged with a first side of a test panel and the second and fourth rollers may be engaged with a second side of the test panel. The first and second roller assemblies are pivoted in opposing directions to bend the panel. A deflection sensor mounted on a movable manipulator measures the deflection of the panel as the panel is bent.

39 Claims, 6 Drawing Sheets

PANEL BENDING AND TESTING DEVICE

FIELD OF THE INVENTION

The present invention relates to test fixtures, and more particularly to fixtures adapted to test a panel of material.

BACKGROUND OF THE INVENTION

Mechanical testing devices for determining mechanical properties of materials are known in the art. Conventional devices exist that are configured to apply a controlled load to a test specimen, while simultaneously recording the deflection or displacement of the specimen as the load is applied. Taking into account the size and shape of the specimen as well as the load characteristics and magnitude, a stress-level can be determined for the test specimen. Once the stress-level is determined, it may be combined with the deflection data recorded during the test and a modulus can be determined for the material. While the particular test methods and units for determining the moduli of various materials may vary, similar insights into the performance characteristics (e.g. maximum load capacity and stiffness) are revealed by the determination of a material's modulus. A properly determined modulus allows accurate structural and mechanical calculations to be performed for a given material. These calculations assist designers and engineers as they implement the material during manufacturing and construction projects.

Increased use of pre-fabricated structural materials such as plywood, plasterboard, composite floor joists and the like has resulted in a greater desire for material property data for these types of products. In addition, the size (e.g. thickness) and strength of certain of these products has increased dramatically in recent years. As such, a testing device that is relatively simple to use, provides accurate data for material modulus determination, and is suitable for use with prefabricated structural materials would be welcomed by those in the art.

SUMMARY OF THE INVENTION

According to the present invention, a panel testing device for testing a panel of material, the panel having first and second sides, includes a frame and a first roller assembly that is pivotally mounted to the frame. The first roller assembly includes a first roller engageable with the first side of the panel and having a first axis. The first roller assembly also includes a second roller engageable with the second side of the panel and having a second axis. The second axis is spaced apart from and is substantially parallel to the first axis. The panel testing device also includes a second roller assembly that is pivotally mounted to the frame and has a third roller engageable with the first side of the panel and having a third axis. The second roller assembly further includes a fourth roller engageable with the second side of the panel and having a fourth axis that is spaced apart from and is substantially parallel to the third axis. The third axis is also substantially parallel to the first axis such that the first, second, third, and fourth axes are all substantially parallel to each other.

The panel testing device also includes a manipulator having an end. The end supports a displacement sensor and is movable between a stowed position and a test position. The displacement sensor is engageable with the panel when the end is in the test position such that the displacement sensor is operable to measure a deflection of the panel.

The present invention also provides a method for testing a panel of material. The method includes providing a panel testing device that is configured to bend a test panel and inserting the test panel into the testing device. The method also includes providing a manipulator that supports a sensor and operating the manipulator to position the displacement sensor against the test panel. The test panel is then bent by the panel testing device, while the deflection of a portion of the test panel is measured with the displacement sensor.

The present invention further provides a measurement device for measuring the deflection of the panel as the panel is bent by the panel bending device. The measurement device includes a deflection measurement assembly that is engageable with the panel and operable to measure the deflection of the panel. A pneumatic actuator is coupled to the panel bending device and supports the deflection measurement assembly. The pneumatic actuator is movable between an extended position and a retracted position and is also operable to provide a biasing force that urges the deflection measurement assembly into engagement with the panel. The biasing force has a magnitude that substantially corresponds to a fluid pressure within the pneumatic actuator. A pressure regulator is coupled to the pneumatic actuator and is operable to maintain the fluid pressure at a substantially constant value, such that the biasing force is maintained at a substantially constant magnitude as the panel is bent.

In preferred embodiments, the panel testing device includes a shield that extends from the frame and surrounds the first and second roller assemblies and the manipulator. The displacement sensor includes two panel engaging tips that are spaced from each other and that define a sensing axis, as well as a third panel engaging tip positioned between the two panel engaging tips and lying on the sensing axis. Thus, as the panel is bent, the third panel engaging tip is displaced away from the sensing axis such that the displacement sensor measures the displacement of the third tip away from the sensing axis. Preferably, the sensing axis is substantially perpendicular to the first axis.

In preferred embodiments, the panel testing device also includes at least one load sensor engaging one of the rollers. The load sensor measures a portion of the load that is applied to the panel as the roller assemblies pivot. Preferably, the first and third axes are substantially stationary as the roller assemblies pivot. The first axis is substantially vertical and a cross brace that substantially maintains a fixed distance between the first and second roller assemblies is provided. During testing, the panel is bent to a first bent position and maintained in the first bent position. The end of the manipulator is then moved to the stowed position to protect the displacement sensor from debris as the panel is further bent beyond the first bent position to failure.

In preferred embodiments, the testing method includes holding the test panel in a bent configuration and operating the manipulator to position the displacement sensor behind a shroud. The test panel is then further bent until the test panel at least partially fractures. A bending load that is applied to the panel by the testing device is also measured as the panel is bent. The modulus of the panel is subsequently calculated using the measured deflection and the measured bending load. Preferably, the panel is subjected to a four-point bending load by the panel bending machine.

Other features and advantages of the invention will become apparent to those skilled in the art upon review of the following detailed description and drawings.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENT

Figure 1:
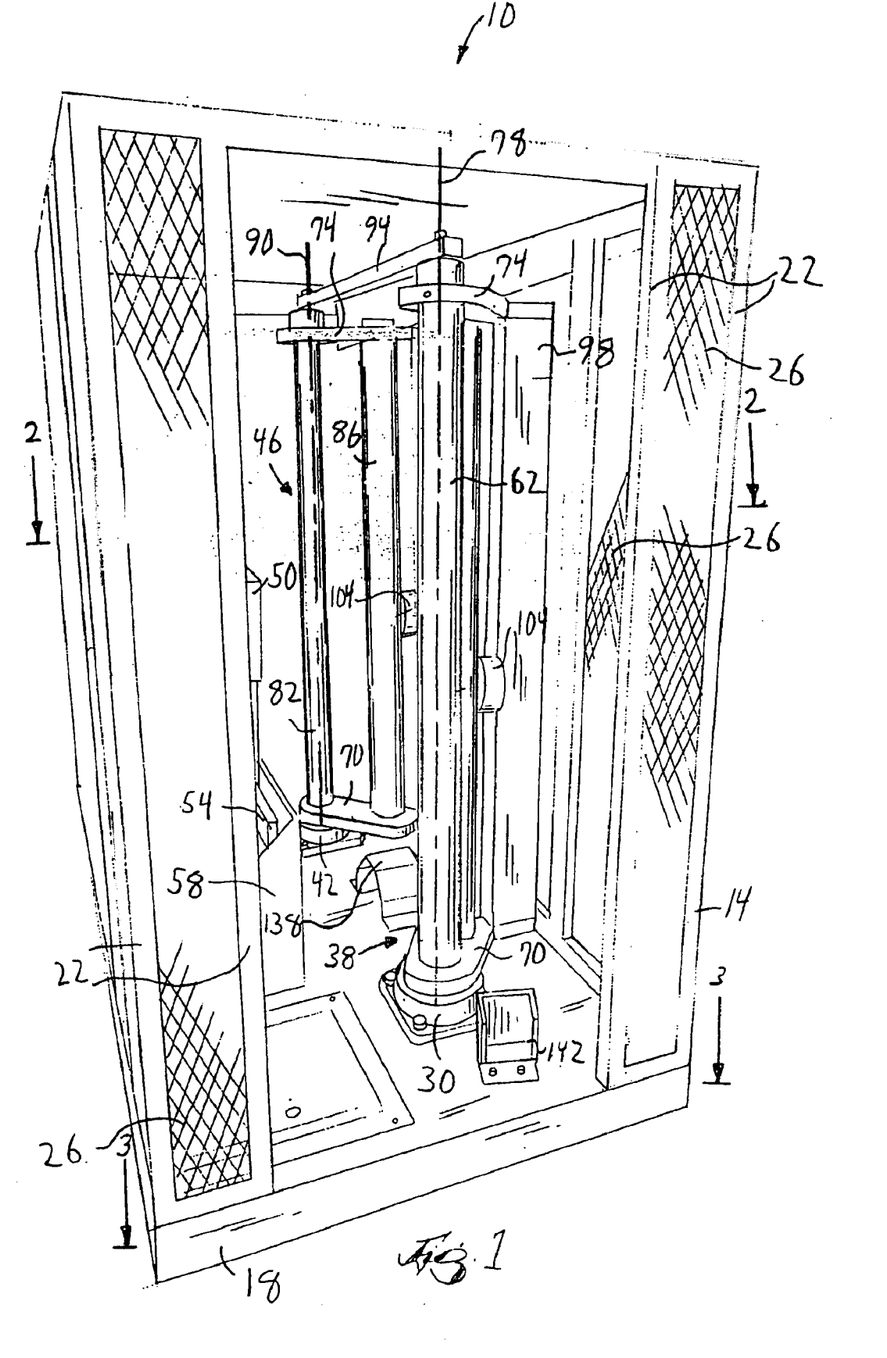
FIG. 1 is a perspective view of a panel testing device according to the present invention.

Referring to FIG. 1, a panel bending and testing device 10 according to the present invention is illustrated. The device 10 includes a structural frame 14 including a base portion 18 and a plurality of uprights 22 extending upwardly from the base portion 18. Mesh sections 26 extend between the uprights 22 to surround at least a portion of the device 10 and serve as debris shields in a manner described further below. A first bearing assembly 30 is secured to the base portion 18 and rotatably supports a first roller assembly 38. A second bearing assembly 42 is similarly secured to the base portion 18 and rotatably supports a second roller assembly 46. A manipulator 50 is secured to the base portion 18 and is illustrated in a stowed position in FIG. 1. In the stowed position, a deflection measurement assembly 54 supported by the manipulator 50 is positioned such that a shroud 58 is between the measurement assembly 54 and the first and second roller assemblies 38, 46 for reasons discussed further below.

Figure 2:
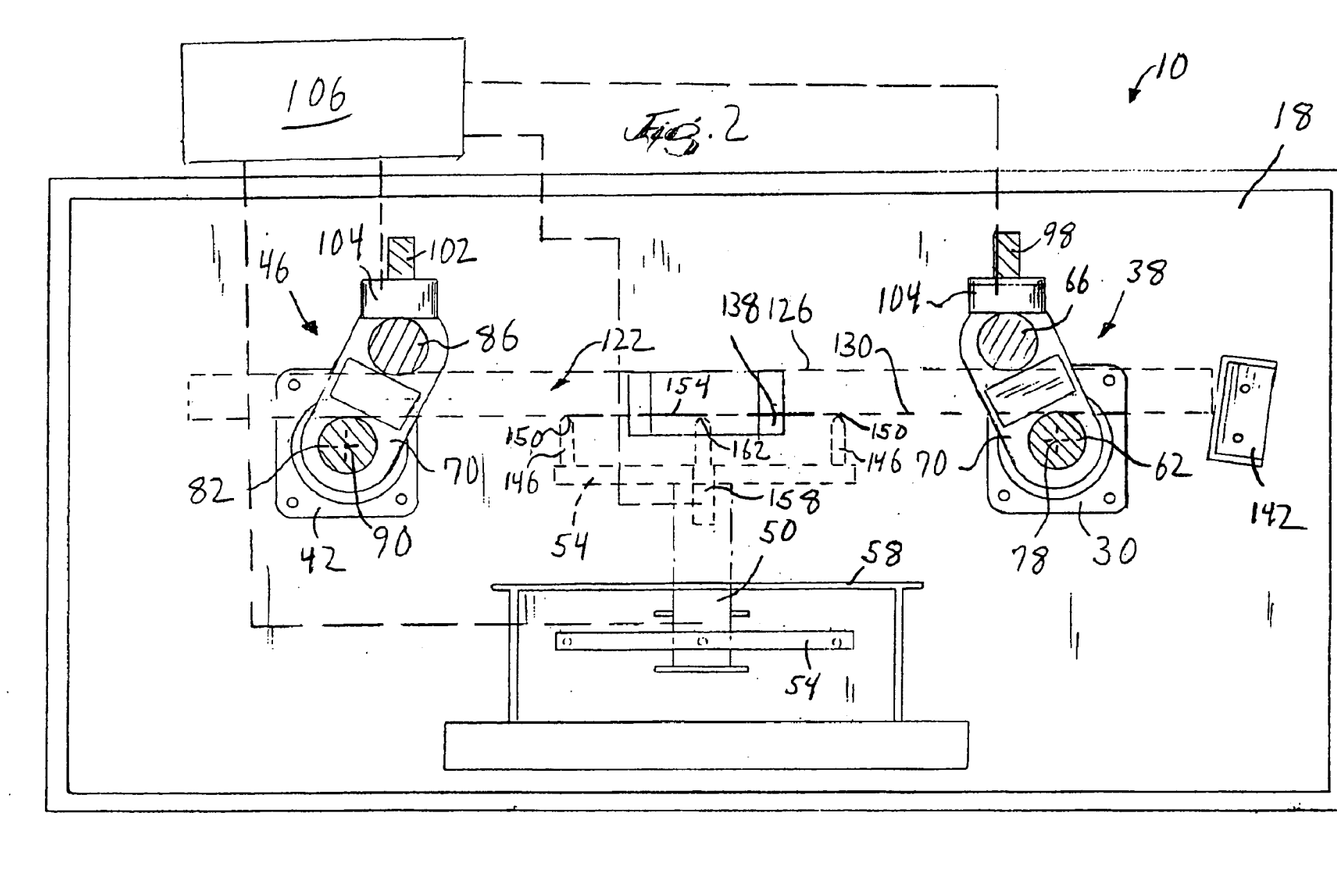
FIG. 2 is a section view taken along line 2—2 of FIG. 1.

Referring now also to FIG. 2, the first roller assembly 38 includes a first roller 62 and a second roller 66 spaced from the first roller 62. The first and second rollers 62, 66 are joined to each other by a lower end plate 70, and an upper end plate 74 (see FIG. 1). A portion of the first roller assembly 38 extends through the first bearing assembly 30 and into the base portion 18. The first roller assembly 38 rotates about a first axis 78 by a hydraulic actuating assembly 80 (see FIG. 3) that is housed within the base portion 18 and will be described further below. As illustrated, the first axis 78, about which the roller assembly 38 rotates, is substantially aligned with the first roller 62. In alternative embodiments, the first roller assembly 38 may be rotated about an axis that is not necessarily aligned with the first roller 62.

The second roller assembly 46 includes a third roller 82 and a fourth roller 86 that are also coupled to each other by lower and upper end plates 70, 74. The third and fourth rollers 82, 86 are structured and configured in substantially the same way as the first and second rollers 62, 66, with the exception that the third and fourth rollers 82, 86 rotate about a second axis 90 in a direction opposite the first and second rollers 62, 66. An upper cross-member 94 (see FIG. 1) couples the upper ends of the first and second rollers assemblies 38, 46 to each other, while allowing each roller assembly to rotate about the first and second axes 78, 90, respectively. Also supported between the upper and lower end plates 74, 70 of the roller assemblies 38, 46 are reaction bars 98 and 102. The reaction bars 98, 102 are spaced from the second and fourth rollers 66, 86 and each reaction bar 98, 102 supports a load sensor in the form of an axial load cell 104. One of the load cells 104 is between the reaction bar 98 and the second roller 66 and the other load cell 104 is between the reaction bar 102 and the fourth roller 86. The load cells 104 provide reaction load measurements that are subsequently used to calculate the strength and stiffness properties of the test panel.

The device 10 also includes a control system 106. As illustrated, the control system 106 communicates with, among other things, the manipulator 50, the deflection measurement assembly 54, and the load cells 104. The control system 106 is provided to control the operation of the device 10 and to record the measurements (e.g. deflection and load) that are generated during such operation. The control system 106 may be in the form of a desktop computer or other types of control systems that would be suitable for use with the present invention, and will be readily apparent to those of ordinary skill in the art.

Figure 3:
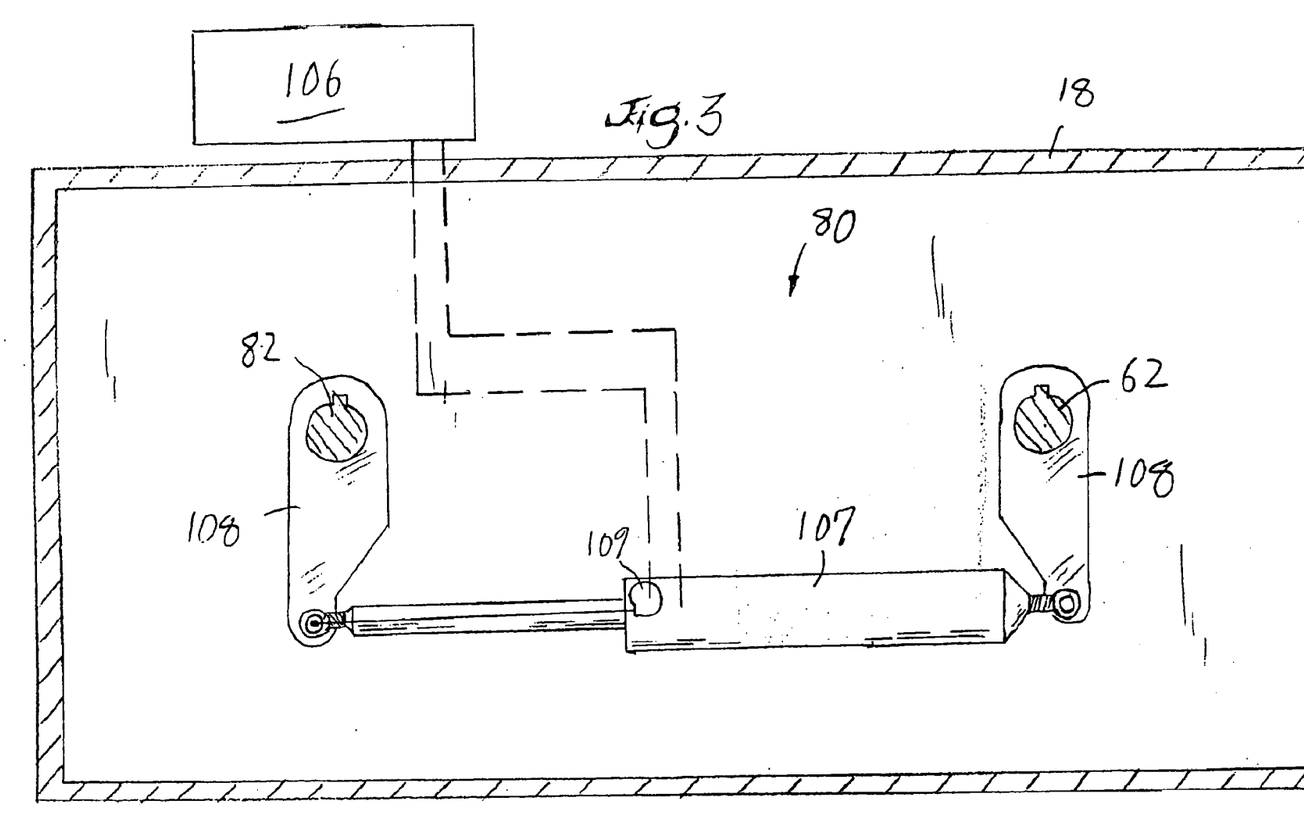
FIG. 3 is a section view taken along line 3—3 of FIG. 1.

Referring to FIG. 3, the hydraulic actuating assembly 80 includes an actuator 107 and a pair of reaction arms 108 that are coupled to the first and second roller assemblies 38, 46. In the illustrated embodiment, the reaction arms 108 are coupled to end portions of the first and third rollers 62, 82 that extend through the bearing assemblies 30, 42. The hydraulic actuator assembly 80 also includes an optical rotary encoder 109 that communicates with the control system 106 and is operable to determine the relative position of each roller assembly 38, 46. One example of a suitable rotary encoder 109 is the JX-EP Series optical encoder available from UniMeasure Inc. of Corvallis Oreg., but other devices for determining the relative positions of the roller assemblies 38, 46 may be used, as will be readily apparent to those of ordinary skill in the art. In operation, the actuator 107 extends or retracts in response to signals provided by the control system 106, thereby rotating the first and second roller assemblies 38, 46. While the illustrated embodiment of the invention includes a hydraulic actuator, as will be readily apparent to those of ordinary skill in the art, other actuating mechanisms including pneumatic, electric, or manual actuation mechanisms may be used as well.

Figure 4:
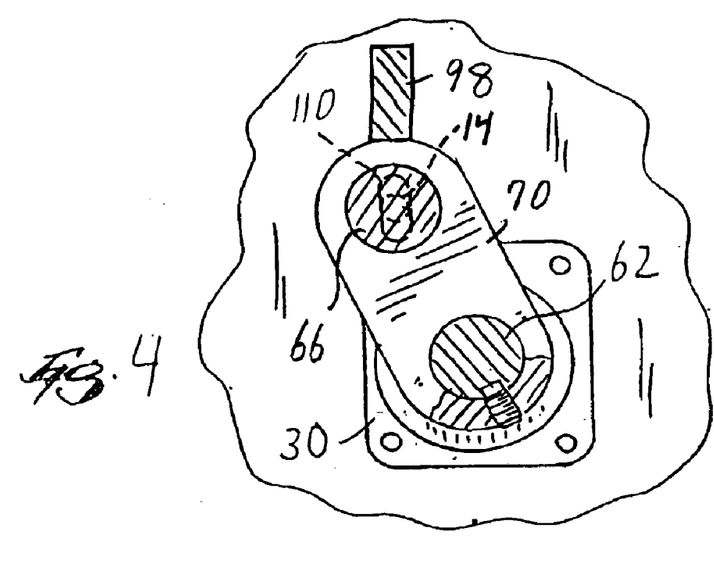
FIG. 4 is an enlarged view of a portion of the panel testing device of FIG. 1.

Referring to FIG. 4, the upper and lower end plates 74, 70 (only the lower end plate 70 being shown in FIG. 4) each include an elongated slot 110. The slot 110 receives a pin portion 114 of the second or fourth roller 66, 86 such that the roller 66, 86 is movable both toward and away from its associated reaction bar 98, 102. As the rollers 66, 86 move toward the reaction bars 98, 102, the rollers 66, 86 engage the load cells 104.

Figure 5:
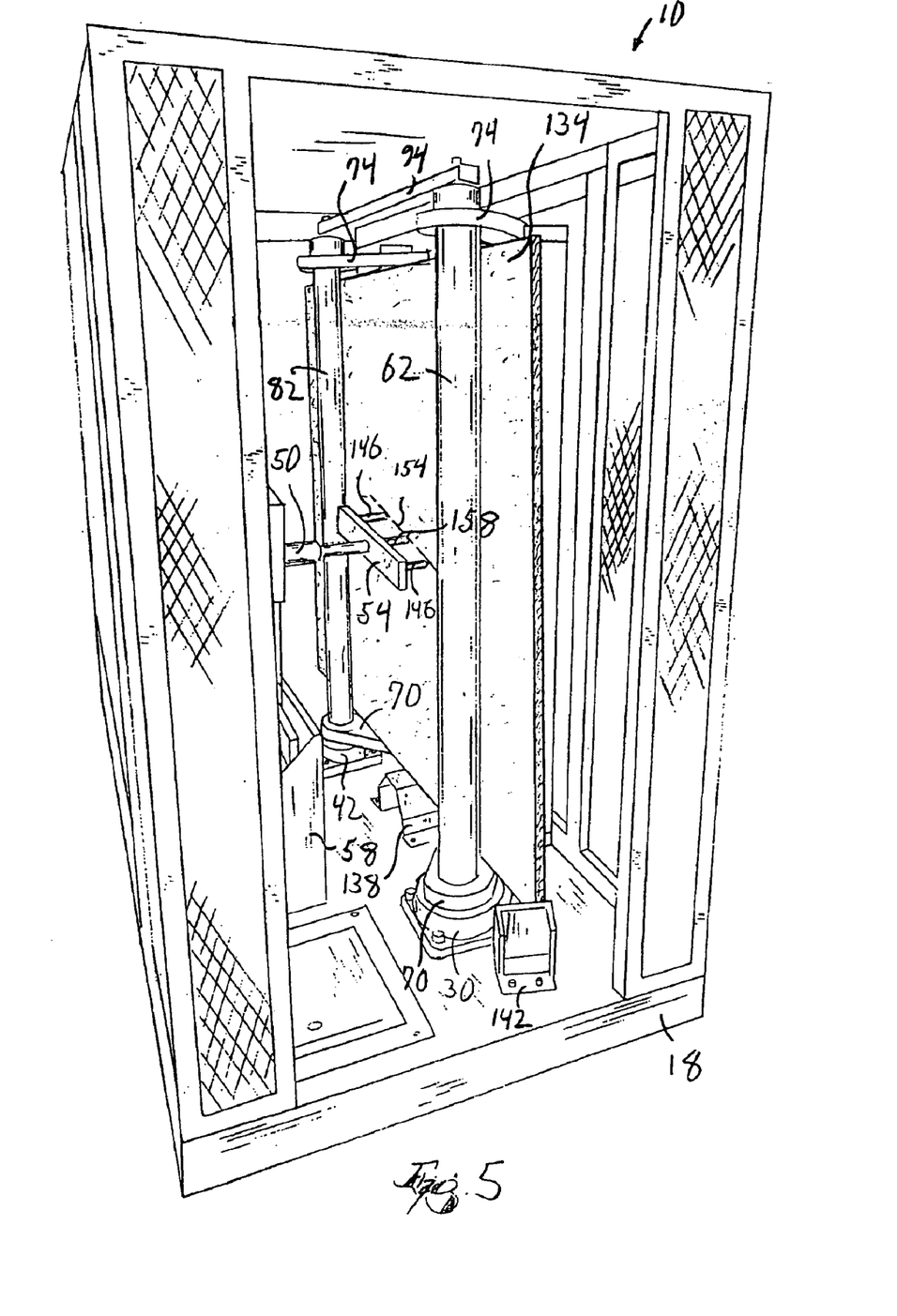
FIG. 5 is a perspective view of the panel testing device of FIG. 1 including a test panel.

Referring to FIGS. 2 and 5, a testing zone 122 is defined between an input plane 126 that is tangent to the second and fourth rollers 66, 86, and an output plane 130 that is tangent to the first and third rollers 62, 82. A test panel 134 is insertable into the testing zone 122 such that the panel is supported by the lower end plates 70 and a lower support bracket 138 that is secured to the base 18. The test panel 122 also abuts an end bracket 142 for proper positioning within the testing zone 118.

The deflection measurement assembly 54 is supported by the manipulator 50 and is movable between the stowed position and a test position. In the illustrated embodiment, the manipulator comprises a pneumatic actuator, described further below, and operates in response to signals provided by the control system 106. While the illustrated manipulator includes a pneumatic actuator, it should be appreciated that substantially any device or linkage arrangement that controls the motion of the deflection measurement assembly 54 may be used in accordance with the teachings of the present invention. In this respect, the manipulator 50 may include fluid operated actuators including pneumatically and hydraulically operated actuators, as well as electrical actuators. While several types and styles of actuators are suitable for use with the present invention, one example of a suitable actuator is the Bimba PneuMoment™ pneumatic actuator available from Bimba Manufacturing Company of Monee Ill.

The measurement assembly 54 includes a pair of outer panel engaging members 146 having tips 150. The outer engaging members 146 are substantially rigid and a sensing axis 154 extends through the tips 150 of the outer panel engaging members 146. As illustrated, the sensing axis 154 is generally perpendicular to the first and second axes 78, 90. The measurement assembly 54 also includes a deflection sensor 158 positioned between the outer engaging members 146 and including a sensor tip 162. The sensor tip 162 is movable with respect to the sensing axis 154 and the sensor 158 is configured to measure a deflection magnitude of the sensor tip 162 away from the sensing axis 154. In preferred embodiments of the invention, the sensor 158 comprises an optical linear encoder such as the Heidenhain-Specto Length Gauge, model no. ST 1271 available from Heidenhain of Traunreut Germany. However, as will be readily apparent to those of ordinary skill in the art, other types of sensors may be used in accordance with the present invention.

Figure 6:
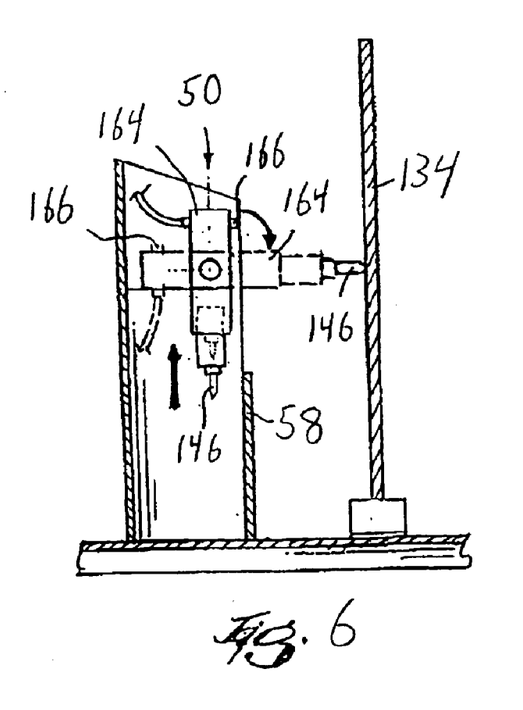
FIG. 6 is a side view of a portion of the panel testing device of FIG. 1.

Referring to FIGS. 2 and 6, the manipulator 50 is configured to move the deflection measurement assembly 54 between the stowed position (illustrated in solid lines) and the test position (illustrated in phantom). When the measurement assembly 54 is in the stowed position, the sensor 158 and the outer engaging members 146 are positioned behind the shroud 58 such that the sensor 158 and the members 146 are shielded from debris that may be created during device operation. When the measurement assembly 54 is in the test position, the sensor tip 162 and the tips 150 are engaged with the test panel 134. In the illustrated embodiment wherein the manipulator 50 includes a pneumatic actuator 164, the manipulator 50 is configured to provide a substantially constant biasing force urging the measurement assembly 54 into engagement with the panel 134. Specifically, the manipulator 50 includes a pressure regulator 166 that is coupled to the pneumatic actuator 164 and regulates the pressure within the actuator 164 during operation of the device 10. When the manipulator 50 moves the measurement assembly 54 to the test position, pressure within the pneumatic actuator 164 is increased to a predetermined value such that the actuator 164 extends or elongates, thereby engaging the member tips 150 and the sensor tip 162 with the panel. The pneumatic actuator 164 is also retractable to disengage the member tips 150 and the sensor tip 162 from the panel. As the panel is bent toward the manipulator 50, the sensing axis 154 is moved toward the manipulator 50, thereby shortening the length of the pneumatic actuator 164. As the pneumatic actuator 164 is shortened, the pressure regulator 166 allows some of the air within the pneumatic actuator 164 to be released to the surroundings such that the pressure within the pneumatic actuator 164 remains substantially constant. Those of ordinary skill in the art will readily appreciate that the biasing force is a direct function of the pressure within the actuator. As a result, maintaining the pressure at a substantially constant value maintains the biasing force at a substantially constant value. Thus, regardless of the length or state of relative extension/retraction of the pneumatic actuator 164 during the test procedure, the biasing force urging the measurement assembly 54 against the panel 134 remains substantially the same. It is preferred that the biasing force have a magnitude that is several times less than the magnitude of the forces required to bend the panel 134. In this respect, measurement errors due to the additional load applied to the panel by the pneumatic actuator 164 will be reduced. While it will be readily apparent to those of ordinary skill in the art that a variety of pressure regulators are suitable for use with the present invention, Arrow Pneumatics, Inc. of Broadview Ill. supplies suitable pressure regulators, available as model nos. R161-R162.

Figure 7:
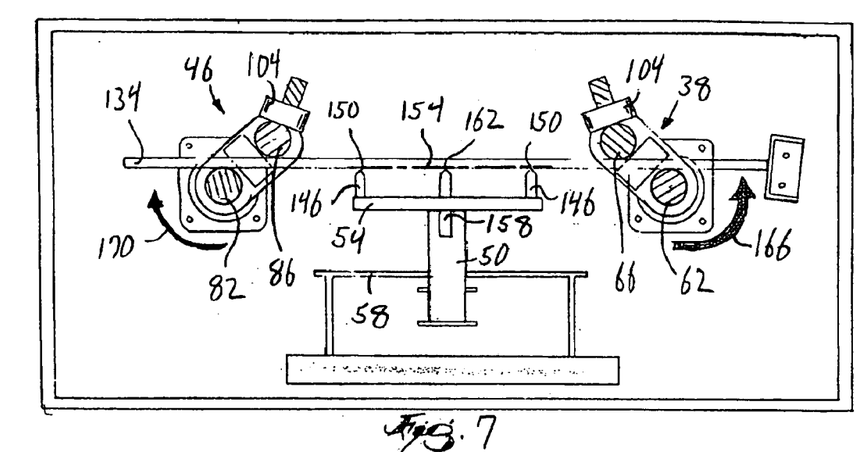
FIG. 7 is a top view of the panel testing device of FIG. 5 prior to a panel test.
Figure 8:
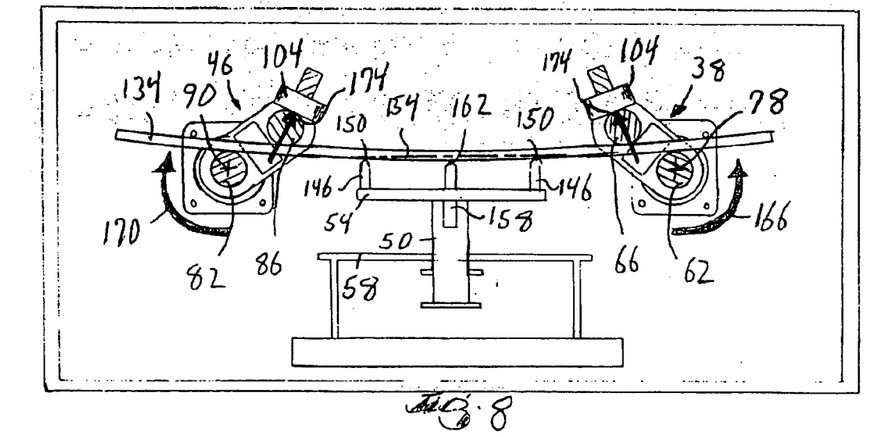
FIG. 8 is a top view of the panel testing device of FIG. 5 during a portion of the panel test.
Figure 9:
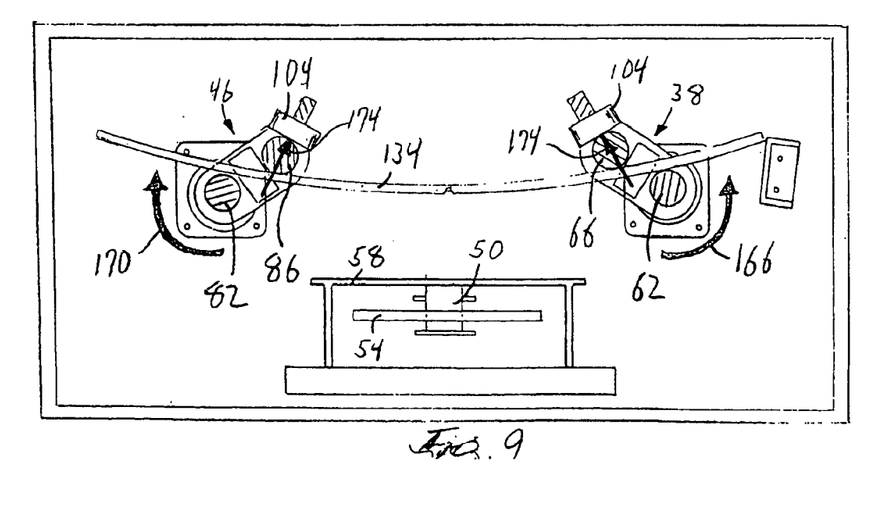
FIG. 9 is a top view of the panel testing device of FIG. 5 near the completion of the panel test.

Referring now to FIGS. 7 through 9, the operation of the device 10 through a complete test cycle is illustrated. With the test panel 134 inserted into the testing zone 122 (see FIG. 2), the control system 106 signals the actuator 107 (FIG. 3) to extend, thereby rotating the first roller assembly 38 in a counter-clockwise direction 166 and the second roller assembly 46 in a clockwise direction 170. As a result, the first and third rollers 62, 82 engage one side of the test panel 134 and the second and fourth rollers 66, 86 engage an opposite side of the test panel 134. As the second and fourth rollers 66, 86 engage the test panel 134 the rollers 66, 86 moved toward the reaction bars 98, 102 and engage the load cells 104, which subsequently send load data to the control system 106. By receiving a non-zero load reading from the load cells 104, the control system 106 is able to determine that the test panel 134 is securely engaged on each side by the rollers 62, 66, 82, and 86.

As illustrated in FIG. 7, the control system configures the roller assemblies 38, 46 such that the test panel 134 is held securely by the device 10, but is not bent or otherwise deflected. Once the panel 134 is in place, the control system 106 signals the manipulator 50, which subsequently moves the deflection measurement assembly 54 to the test position such that the tips 150 and the sensor tip 162 engage the test panel. Note that prior to initiation of the test cycle, the sensor tip 162 is substantially aligned with the sensing axis 154.

Referring to FIG. 8, the first and second roller assemblies 38, 46 are rotated about the first and second axes 78, 90, respectively by the actuator 107 such that the test panel 134 is bent or deflected about a bending axis (not shown) toward a first bent position. As the test panel 134 is bent, the second and fourth rollers 66, 86 are urged toward the reaction bars 98, 102 due to resistance provided by the panel 134. The second and fourth rollers 66, 86 slide within the slots 110 (shown in FIG. 3) and press against the load cells 104 such that substantially all the resistance to bending provided by the panel is counteracted by the load cells 104. In this respect, the load cells 104 are able to measure the magnitude of a bending or resisting force 174 provided by the panel 134 as the panel 134 is bent due to the rotation of the first and second roller assemblies 38, 46. Simultaneously, the sensor tip 162 is deflected away from the sensing axis 154 and the sensor 158 measures the magnitude of the deflection of the sensor tip 162. The measurements taken by both the load cells 104 and the sensor 158 are recorded by the control system 106 for further processing in order to determine the strength and stiffness of the test panel 134.

Once the panel 134 has been bent to the first bent position, the control system 106 halts the rotation of the first and second roller assemblies 38, 46 and signals the manipulator 50 to move the deflection measurement assembly 54 to the stowed position. In this respect, the pressure within the pneumatic actuator 164 is reduced such that the actuator 164 retracts and is subsequently rotated toward the stowed position. Once the measurement assembly 54 is behind the shroud 58, the roller assemblies 38, 46 are further rotated and the panel 134 is further bent until it begins to fracture or crack (illustrated in FIG. 9). As the panel fractures, the load cells 104 continue to measure the resisting force provided by the panel 134. The shroud 58 protects the deflection measurement assembly 54 from any debris that is created while the panel 134 fractures, thereby preventing damage to the sensor 158. Additionally, the mesh sections 26 substantially reduce the expulsion of debris, as well as the panel 134 and broken panel portions, from the device 10.

While the illustrated embodiment measures the load applied to the panel using the two load cells 104, it will be readily apparent to those of ordinary skill in the art that the load applied to the panel can be measured or otherwise detected in various ways. For example, a single load cell may be positioned between the hydraulic cylinder 107 and one of the reaction arms 108, the load applied to the panel would then be calculated using known engineering formulas. Other embodiments of the invention may include rotational torque sensors intercoupled between the reaction arms 108 and the first and third rollers 62, 82. Such sensors generally measure the torque applied to the panel 134 by each roller assembly 38, 46 as the roller assemblies 38, 46 are rotated. Again, the resulting load applied to the panel 134 is calculated using known engineering equations. In addition, there are various other techniques for measuring or otherwise calculating the load applied to the panel 134 as the panel is bent, which will be readily apparent to those of ordinary skill in the art.

As described above, the control system 106 preferably controls substantially all aspects of the testing operations including operation of the hydraulic actuating assembly 80 to rotate the roller assemblies 38, 46, movement of the manipulator 50 between the stowed and test positions, and recordation of the load magnitudes measured by the load cells 104 and the deflection magnitude measured by the sensor 158. Preferably, the system 106 records the load and deflection magnitudes throughout the testing process such that the load and deflection data may be utilized to generate useful material property parameters that assist designers and engineers in the utilization of the test panel 134.

Various features of the invention are set forth in the following claims.

What is claimed is:

1. A panel testing device for testing a panel having a first side and a second side, the panel testing device comprising:
   a frame;
   a first roller assembly pivotally mounted to the frame and including a first roller engageable with the first side and having a first axis, and a second roller engageable with the second side and having a second axis that is spaced from and substantially parallel to the first axis;
   a second roller assembly pivotally mounted to the frame and including a third roller engageable with the first side and having a third axis substantially parallel to the first axis, and a fourth roller engageable with the second side and having a fourth axis spaced from and substantially parallel to the third axis, the first and second roller assemblies being pivotable in opposing directions to bend the panel; and
   a manipulator having an end, the end supporting a deflection sensor and being movable between a stowed position and a test position, the sensor being engageable with the panel when the end is in the test position to measure a deflection of the panel.

2. The panel testing device of claim 1 further comprising a shield extending from the frame and surrounding the first and second roller assemblies and the manipulator.

3. The panel testing device of claim 1, wherein the deflection sensor includes two panel engaging tips spaced from each other and defining a sensing axis, and a third panel engaging tip between the two panel engaging tips and lying on the sensing axis, and wherein as the panel is bent the third panel engaging tip is displaced away from the sensing axis.

4. The panel testing device of claim 3, wherein the sensor measures the displacement of the third tip away from the sensing axis.

5. The panel testing device of claim 3, wherein the sensing axis is substantially perpendicular to the first axis.

6. The panel testing device of claim 1 further comprising a load sensor engaging one of the rollers, wherein the load sensor measures at least a portion of a bending load that is applied to the panel as the roller assembly pivots.

7. The panel testing device of claim 1, wherein the first and third axes are substantially stationary with respect to the frame as the roller assemblies pivot.

8. The panel testing device of claim 1, wherein the first axis is substantially vertical.

9. The panel testing device of claim 1 further comprising a cross member extending between the first and second roller assemblies.

10. The panel testing device of claim 1, wherein the panel is bent to a first bent position and maintained in the first bent position, and wherein prior to bending the panel beyond the first bent position, the end is moved to the stowed position.

11. The panel testing device of claim 1, further comprising an actuating assembly operable to pivot the first and second roller assemblies, and a control system, the control system communicating with the actuating assembly and the manipulator for controlled operation thereof and receiving signals from the deflection sensor.

12. A method for testing a panel of material, the method comprising:
   providing a panel testing device configured to bend a test panel;
   inserting the test panel into the testing device;
   providing a manipulator having an end that supports a deflection sensor;
   operating the manipulator to position the sensor against the test panel;
   bending the test panel with the panel testing device; and
   measuring a deflection of a portion of the test panel with the sensor.

13. The method of claim 12 further comprising:
   providing a control system communicating with panel testing device, the manipulator, and the sensor;
   controlling the operation of the device and the manipulator with the control system; and
   sending signals from the sensor to the control system.

14. The method of claim 13 further comprising holding the test panel in a bent configuration, operating the manipulator to position the sensor behind a shroud, and bending the test panel at least until the test panel fractures.

15. The method of claim 13 further comprising measuring a bending load applied to the panel by the testing device as the panel is bent, and calculating a modulus for the panel using the measured deflection and the measured bending load.

16. The method of claim 12, wherein the bending step includes subjecting the panel to a four-point bending load.

17. The method of claim 12 further comprising surrounding the panel testing device with a shield to prevent ejection of the panel from the panel testing machine.

18. The method of claim 12 further comprising supporting a bottom edge of the test panel, and wherein the bending occurs about an axis that is substantially vertical.

19. The method of claim 12, wherein the sensor includes two panel engaging tips spaced from each other and defining a substantially horizontal sensing axis, and a third panel engaging tip between the two panel engaging tips, and wherein bending the panel displaces the third panel engaging tip away from the sensing axis.

20. A measurement device for measuring the deflection of a panel deflected by a panel bending device, the measurement device comprising:

a manipulator;

a pair of panel engaging members supported by the manipulator, each member including a member tip that is engageable with the panel;

a sensor supported by the manipulator and including a sensor tip engageable with the panel;

a first axis extending through the member tips, the sensor being movable with respect to the first axis; and a second axis that is substantially perpendicular to the first axis, the panel bending device operable to bend the panel about the second axis, wherein as the panel is bent, the sensor tip is displaced with respect to the first axis, and wherein the sensor measures the displacement of the sensor tip.

21. The measurement device of claim 20, wherein the manipulator is operable to position the member tips and the sensor tip against the panel before the panel is bent.

22. The measurement device of claim 20, wherein the panel is bent to a first bent position and maintained in the first bent position, and wherein prior to bending the panel beyond the first bent position, the member tips and the sensor tip are moved away from the panel to a stowed position.

23. A panel testing device for testing a panel having a first side and a second side, the panel testing device comprising:

a frame;

a first roller assembly having a first end pivotally mounted to the frame, a second end opposite the first end, a first roller engageable with the first side, and a second roller engageable with the second side and spaced from and substantially parallel to the first roller;

a second roller assembly having a first end pivotally mounted to the frame, a second end opposite the first end, a third roller engageable with the first side, and a fourth roller engageable with the second side and spaced from and substantially parallel to the third roller, the first and second roller assemblies being pivotable in opposing directions to bend the panel;

a deflection sensor engageable with the panel between the first and third rollers and adapted to measure a deflection of the panel as the panel is bent; and a cross member extending between the second ends.

24. The panel testing device of claim 23 further comprising a shield extending from the frame and surrounding the first and second roller assemblies and the sensor.

25. The panel testing device of claim 23, wherein the deflection sensor includes two panel engaging tips spaced from each other and defining a sensing axis, and a third panel engaging tip between the two panel engaging tips, and wherein as the panel is bent the third panel engaging tip is displaced away from the sensing axis.

26. The panel testing device of claim 25, wherein the deflection sensor measures the displacement of the third tip away from the sensing axis.

27. The panel testing device of claim 23 further comprising a load sensor engaging one of the rollers, wherein the load sensor measures at least a portion of a bending load that is applied to the panel as the roller assembly pivots.

28. The panel testing device of claim 23, wherein the first roller is substantially vertical.

29. The panel testing device of claim 23 further comprising a support plate between the first and second roller assemblies and supporting an edge of the test panel.

30. The panel testing device of claim 23, further comprising a manipulator operable to move the sensor between a test position and a stowed position.

31. The panel testing device of claim 30, further comprising an actuating assembly operable to pivot the first and second roller assemblies, and a control system, the control system communicating with the actuating assembly and the manipulator for controlled operation thereof and receiving signals from the deflection sensor.

32. A measurement device for measuring a deflection of a panel as the panel is bent by a panel bending device, the measurement device comprising:

a deflection measurement assembly engageable with the panel and operable to measure the deflection of the panel;

a pneumatic actuator coupled to the panel bending device and supporting the deflection measurement assembly, the pneumatic actuator movable between an extended position and a retracted position and operable to provide a biasing force that urges the deflection measurement assembly into engagement with the panel, the biasing force having a magnitude that substantially corresponds to a fluid pressure within the pneumatic actuator; and a pressure regulator coupled to the pneumatic actuator, the pressure regulator operable to maintain the fluid pressure at a substantially constant value, thereby maintaining the biasing force at a substantially constant magnitude as the panel is bent.

33. The measurement device of claim 32, wherein as the panel is bent the pneumatic actuator is urged toward the retracted position.

34. The measurement device of claim 32, wherein the deflection measurement assembly includes a pair of panel engaging members, the members including member tips that are engageable with the panel and define a first axis that extends through the member tips, and a sensor including a sensor tip engageable with the panel and movable with respect to the first axis.

35. The measurement device of claim 34, further comprising a second axis that is substantially perpendicular to the first axis, the panel bending device operable to bend the panel about the second axis.

36. The measurement device of claim 35, wherein as the panel is bent, the sensor tip is displaced with respect to the first axis, and wherein the sensor measures the displacement of the sensor tip.

37. The measurement device of claim 32, wherein the pneumatic actuator is pivotally coupleable to panel bending device and the deflection measurement assembly is movable between a test position and a stowed position.

38. The measurement device of claim 32 further comprising a control system communicating with the pressure regulator, the pressure regulator adjusting the fluid pressure in response to signals received from the control system.

39. The measurement device of claim 38, where in the control system receives signals from the deflection measurement assembly that correspond to the deflection of the panel.

* * * * *